United States Patent
Policastro et al.

[19]

[11] Patent Number: 5,904,142
[45] Date of Patent: May 18, 1999

[54] DEVICE FOR ESTIMATING CENTRAL VENOUS PRESSURE

[75] Inventors: Dennis C. Policastro, Orchard Park; Robert E. Mates, Buffalo; Kenneth Peebles, Lancaster, all of N.Y.

[73] Assignee: The Research Foundation of State University of New York, Albany, N.Y.

[21] Appl. No.: 08/565,444

[22] Filed: Nov. 30, 1995

[51] Int. Cl.⁶ ..................................................... A61B 5/00
[52] U.S. Cl. ........................... 128/672; 33/262; 128/748
[58] Field of Search ............................. 33/451, 454, 460, 33/354, 262, 809, 472, 473, 371, 372; 128/673, 672

[56] References Cited

U.S. PATENT DOCUMENTS

| | | |
|---|---|---|
| 3,413,970 | 12/1968 | Rockwell . |
| 3,602,214 | 8/1971 | London et al. . |
| 4,204,547 | 5/1980 | Allocca . |
| 4,348,815 | 9/1982 | Hurt ........................................... 33/473 |
| 4,399,616 | 8/1983 | Jansson ...................................... 33/451 |
| 4,451,993 | 6/1984 | Yauk .......................................... 33/451 |
| 4,452,252 | 6/1984 | Sackner . |
| 4,456,015 | 6/1984 | Sackner . |
| 4,554,746 | 11/1985 | Echeverria ................................. 33/473 |
| 4,566,462 | 1/1986 | Janssen . |
| 4,813,149 | 3/1989 | Herkimer ................................... 33/451 |
| 4,986,277 | 1/1991 | Sackner . |
| 5,040,540 | 8/1991 | Sackner . |
| 5,353,509 | 10/1994 | Black ......................................... 33/451 |
| 5,446,969 | 9/1995 | Terenzoni .................................. 33/451 |

FOREIGN PATENT DOCUMENTS

| | | |
|---|---|---|
| 359972 | 3/1990 | European Pat. Off. . |
| 452332 | 12/1974 | U.S.S.R. . |
| 1477377 | 5/1989 | U.S.S.R. . |
| 9222871 | 12/1992 | WIPO . |

OTHER PUBLICATIONS

B. Bates, L. Bickley & R. Hoekelman, A Guide to Physical Examination and History Taking 270 (1995).

J. Constant, Bedside Cardiology 80 (1985).

*Primary Examiner*—Robert L. Nasser
*Attorney, Agent, or Firm*—Robert E. Mates

[57] ABSTRACT

A device capable of providing non-invasive, accurate estimates of central venous pressure. This diagnostic device is particularly useful with patients suffering from cardiac disease.

14 Claims, 5 Drawing Sheets

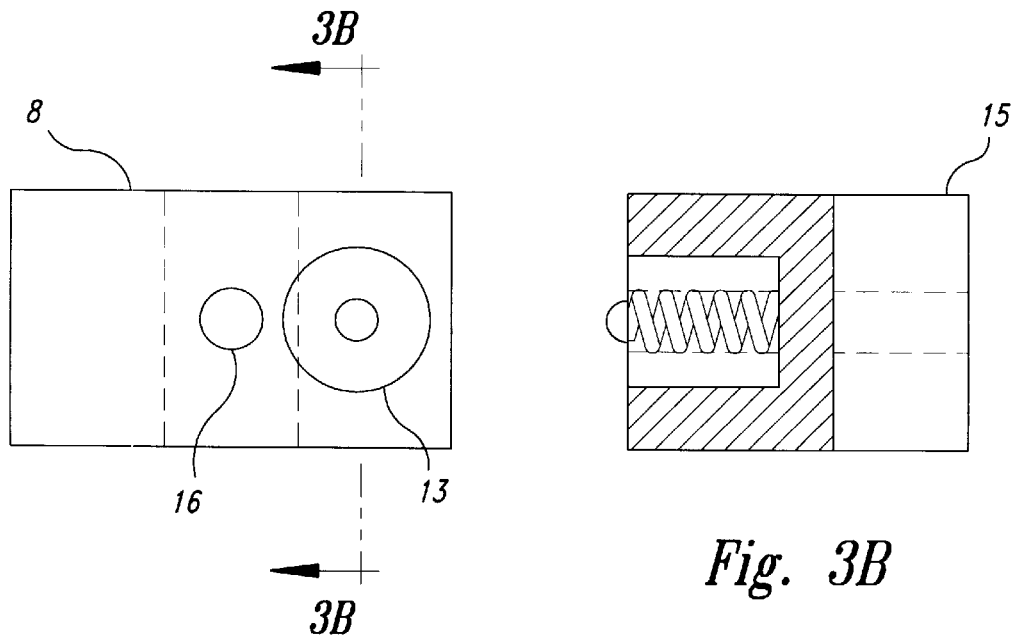
Fig. 3A
Fig. 3B
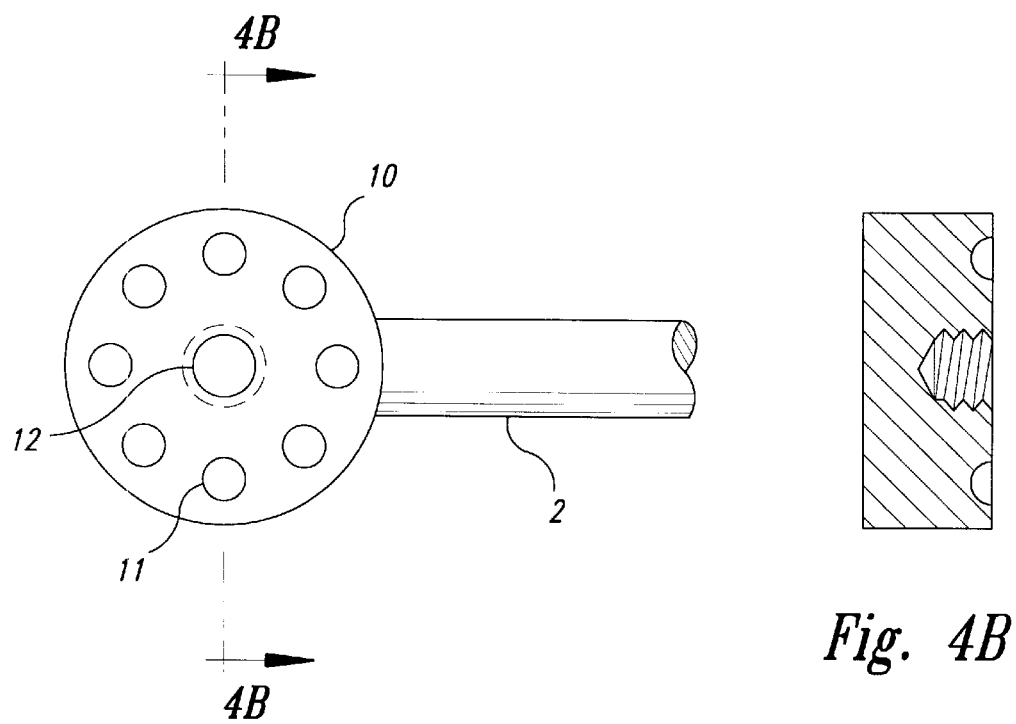
Fig. 4A
Fig. 4B

DEVICE FOR ESTIMATING CENTRAL VENOUS PRESSURE

BACKGROUND OF THE INVENTION

1. Field of the Invention

The present invention relates to a novel device for estimating central venous pressure.

2. Description of the Related Art

An accurate, quick, and non-invasive means for estimating central venous pressure (hereinafter CVP) is a valuable diagnostic tool for patients suffering from cardiac disease. In a patient suffering from cardiac disease the heart fails to pump sufficient volume through the circulatory system, and this causes blood to "back up" in the veins returning blood to the heart. Excess blood volume which is not pumped through by the heart muscle causes blood pressure in the veins, or venous pressure, to increase which results in distension or expansion of the patient's veins.

A precise measurement of CVP, or the blood pressure in the right atrium of the heart, is often necessary for the diagnosis of a patient with cardiac disease. The most reliable and accurate method of measurement involves the insertion of a catheter into one of the major veins in the circulatory system. The catheter is threaded through the vein until it reaches a position near the heart where a pressure measurement is taken. Such a procedure is invasive, medically risky, and highly traumatic for the patient.

Invasive measures which establish CVP are used only when an accurate measurement is absolutely necessary. Non-invasive methods are used when an estimate of CVP is sufficient for diagnosis. A simple method for estimating CVP is described in B. Bates, L. Bickley & R. Hoekelman, A Guide to Physical Examination and History Taking 270–271 (1995) and in J. Constant, Bedside Cardiology 80–86 (1985). The cited pages are incorporated herein by way of reference.

The physiological basis for the method is that in a healthy individual who is standing or sitting the blood pressure in the internal jugular vein, which is located behind the sternomastoid muscle in the neck, is lower than atmospheric pressure because gravity aids the movement of blood toward the heart. The internal jugular vein in this situation is normally partially collapsed. When blood "backs up" in the veins due to cardiac disease the internal jugular vein expands and pulsations in the vein are visible on the surface of the neck. The visible pulsations begin at the base of the neck and progress upward as CVP increases. A measurement of the height of the highest location on the neck where pulsations are visible provides a simple and non-invasive method for estimating CVP. The internal jugular vein is thereby used as a manometer to estimate CVP.

The above-mentioned procedure comprised the following steps: the head of the patient's bed is placed at an elevated angle, pulsations in the internal jugular vein are located, and the highest point at which these pulsations are visible is measured. Conventionally, the height of this point is measured from the sternal angle, also called the angle of Louis, which is a reference point on the sternum. The sternal angle is roughly 5 centimeters above the right atrium. The height measurement is taken by placing the base of a centimeter ruler on the sternal angle while the ruler is held in a vertical orientation. A tongue depressor or other straight object is then placed at a right angle with respect to the ruler and is used to locate the highest visible pulsations. A physician may also merely estimate the height visually. If the highest visible pulsations are more than a specified number of centimeters above the sternal angle then the CVP is considered elevated. A diagram indicating this method is shown in FIG. 5.

Several other methods or devices may be used to estimate CVP. Rockwell, in U.S. Pat. No. 3,413,970, discloses an integral, one piece arm which supports a slidable member. The slidable member is extended to a prescribed position under a patient to establish the vertical position of the patient's superior vena cava, after which a scale on the arm may be used to set a baseline for a manometer. The arm includes a level indicating means afixed thereto. The CVP measurement is invasive. Sackner, in U.S. Pat. Nos. 4,452, 252, 4,456,015, 4,986,277, and 5,040,540, discloses several transducers which are wrapped around a patient's neck to measure changes in the cross-sectional area of the neck. Those changes are related to CVP. Allocca, in U.S. Pat. No. 4,204,547, discloses a method of monitoring intracranial pressure by occluding the jugular vein at a particular point and measuring the rate of change of blood pressure upstream of that point. Soviet Patent No. SU-452332-A discloses the measurement of venous pressure while the patient's inclined position is raised.

The need remains for an accurate and non-invasive method for estimating central venous pressure.

SUMMARY OF THE INVENTION

The object of this invention is to provide a device which enables an accurate and non-invasive estimation of central venous pressure. A device according to the invention is comprised of a substantially straight bar having a bottom portion and a top portion. A graduated scale is afixed to or etched into the surface of the bar beginning approximately at the bottom portion. A pointer comprising a pivoting base, a telescoping member and a distal end is movably attached to said bar at its pivoting end such that the pointer slides along the length of the bar. The pointer further comprises a bubble-type indicator means formed integrally therewith. The distal end of the pointer extends in a straight manner from the bar and is extended by the telescoping member. The pointer is rotatable with respect to the bar such that the angle between the bar and the pointer is adjustable. Detents in the pivoting base fix and hold the pointer at several preset angles.

BRIEF DESCRIPTION OF THE DRAWINGS

FIG. 3A illustrates a top view of the detent bracket;

FIG. 3B illustrates a sectional view of the detent bracket;

FIG. 4A illustrates a side view of the pivoting base of the pointer;

FIG. 4B illustrates a sectional view of the pivoting base of the pointer;

DESCRIPTION OF THE PREFERRED EMBODIMENT

Figure 1:
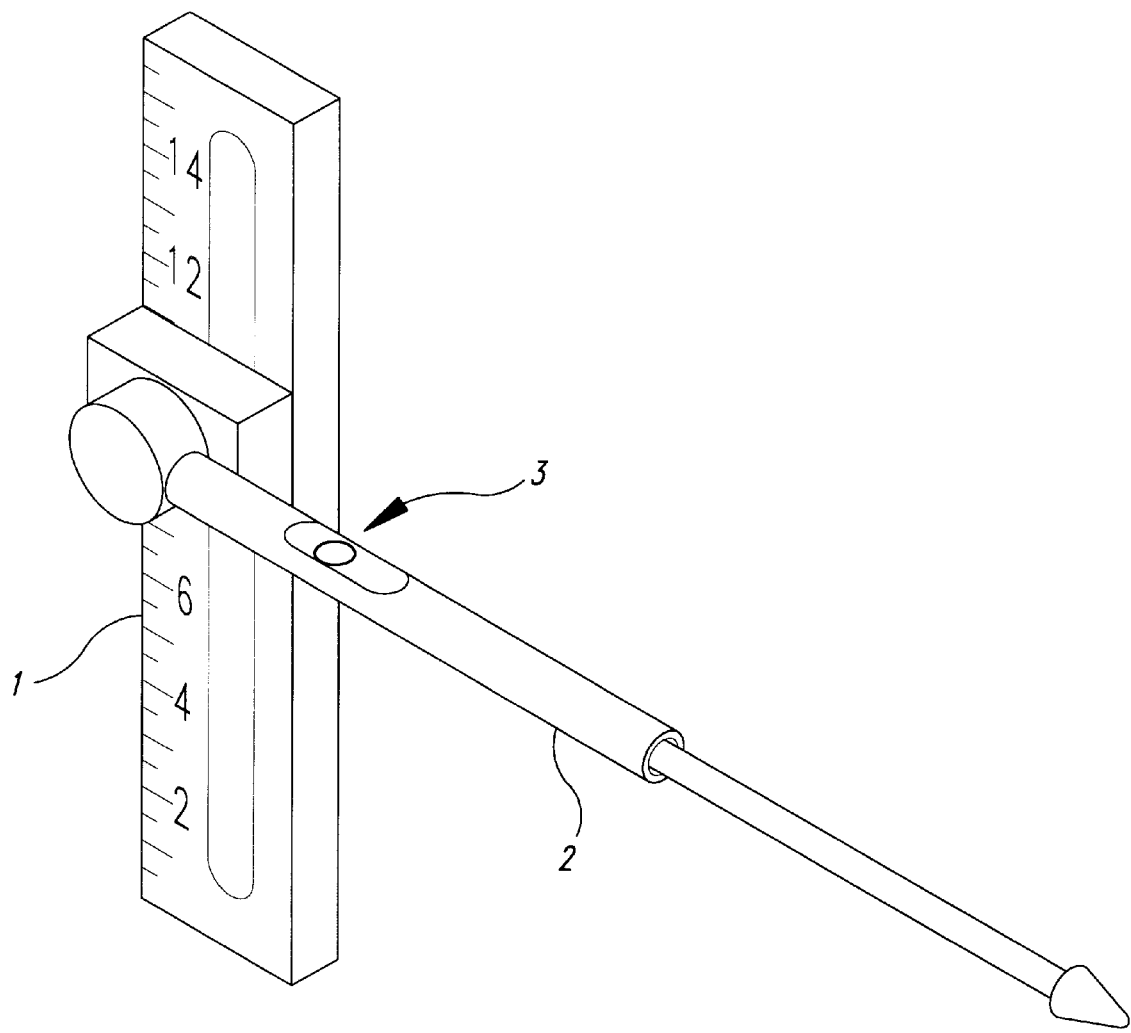
FIG. 1 illustrates a perspective view of the device.

A perspective view of a device according to the invention is shown in FIG. 1. A substantially straight bar 1 supports a telescoping pointer 2 which is rotatably attached to the bar. Bubble-type indicating means 3 is integrally formed within the telescoping pointer.

Figures 2A, 2B:
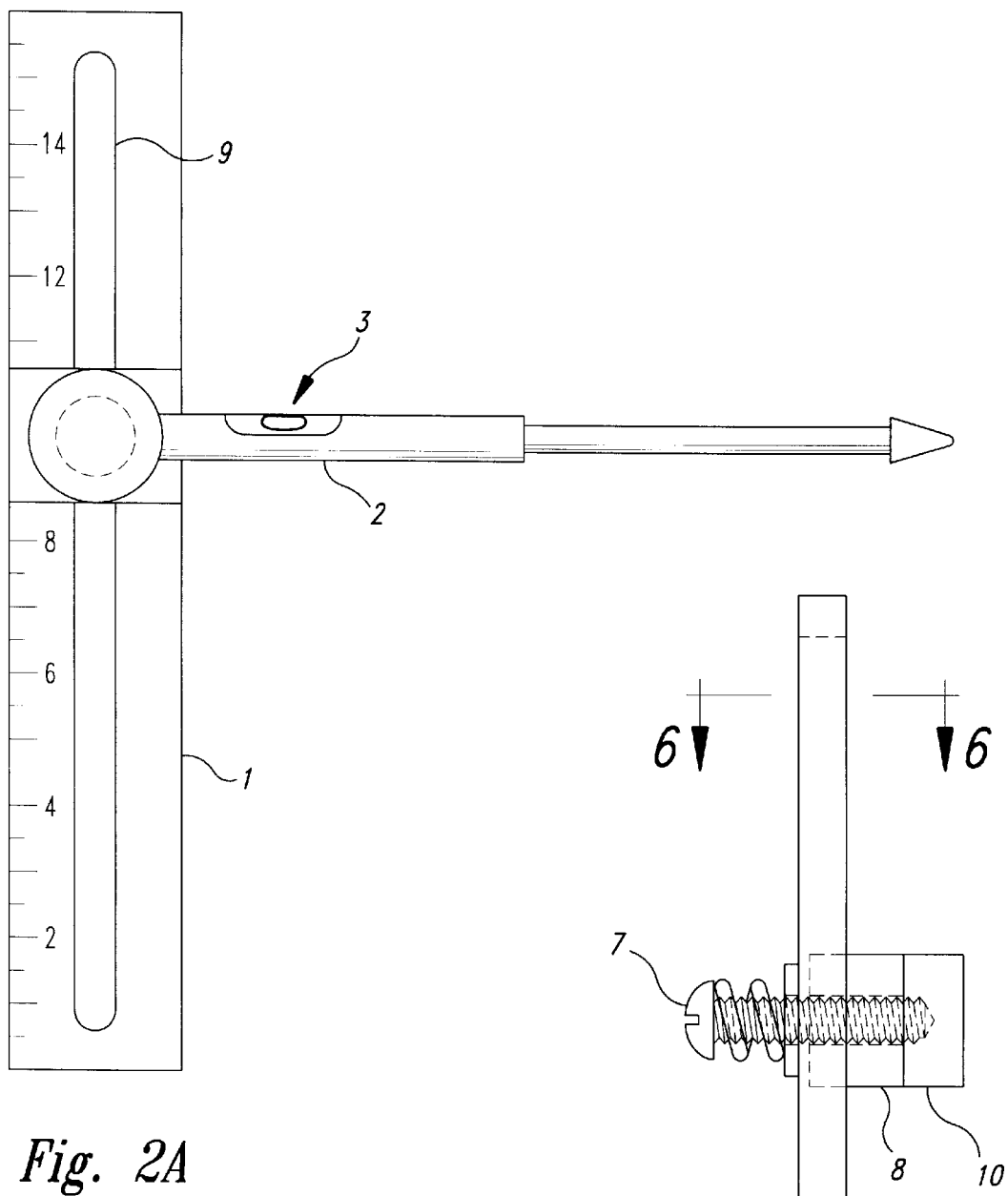
FIG. 2A illustrates a front view of the device.
FIG. 2B illustrates a side view of the device.
Figure 5:
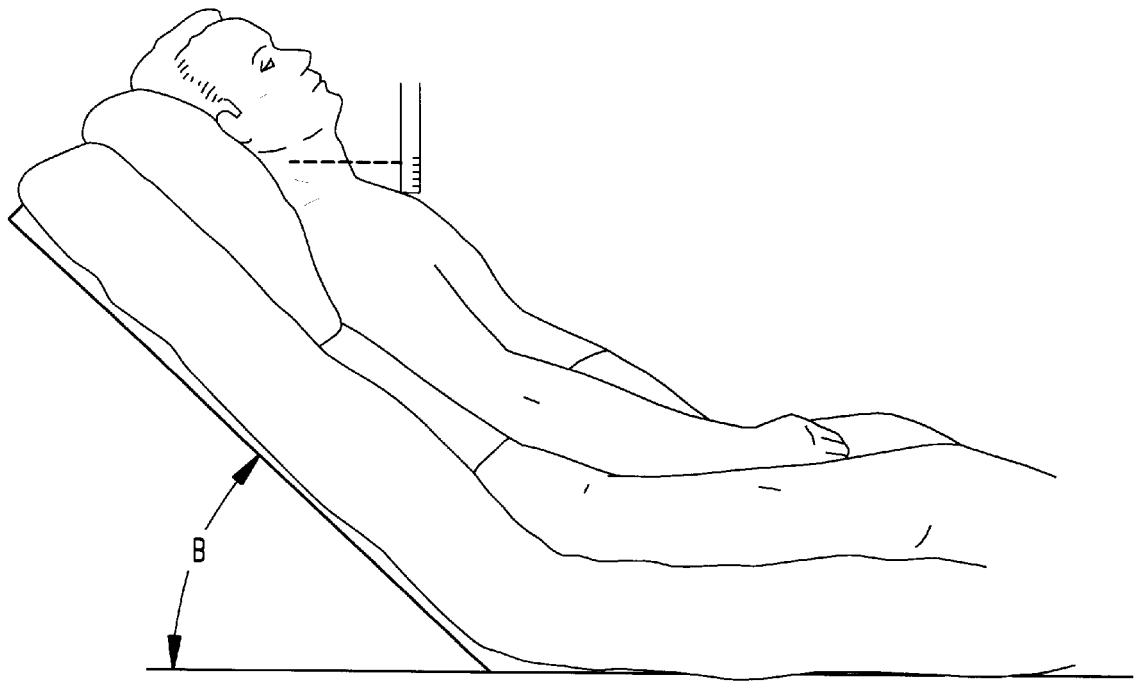
FIG. 5 illustrates the conventional method of estimating central venous pressure in a non-invasive manner.

FIG. 2A shows a front view of the device and FIG. 2B shows a side view of the device. Bar 1 has a slot 9 integrally formed therein, and a graduated scale in centimeters is etched or otherwise permanently affixed to an edge of bar 1. The graduated scale begins at a bottom portion of the bar and increases along the length of the bar toward a top portion.

Pointer 2 is shown in FIG. 1 and FIG. 2A and is comprised of a telescoping member with a distal end, a pivoting base 10, and bubble-type indicating means 3 formed integrally therewith. The bubble-type indicating means indicates when the pointer 2 is in a horizontal position. The telescoping distal portion is comprised of a plurality of interfitting cylinders of progressively decreasing diameter, wherein each adjacent cylinder fits inside the preceding cylinder. The last cylinder extends furthest from the pivoting base and is formed with a blunt cap on the furthest distal end.

Pivoting base 10 shown in FIG. 4A and FIG. 4B has a threaded hole 12 in the center thereof and a plurality of circular depressions 11 spaced equidistantly from the center hole 12 along a circular centerline. The depressions face detent bracket 8 which is slidably positioned in slot 9, shown in FIG. 2A and FIG. 2B. The detent bracket, detailed in FIG. 3A and FIG. 3B, is integrally formed with rudder 15 which intersects slot 9 in slidable fashion such that the detent bracket may slide along the length of bar 1. Detent 13 is formed inside the detent bracket and is comprised of a hole inside the bracket in which a spring is set which forces a ball bearing toward the surface of the detent bracket such that the ball bearing protrudes slightly through the surface of the bracket. When pressure is exerted on the ball bearing against the force of the spring the ball bearing recedes below the surface of the bracket. The ball bearing returns to protrude from the surface when said pressure is released. Detent 13 faces depressions 11 when pivoting base 10 is held against detent bracket 8 as shown in FIG. 2B.

Figure 6:
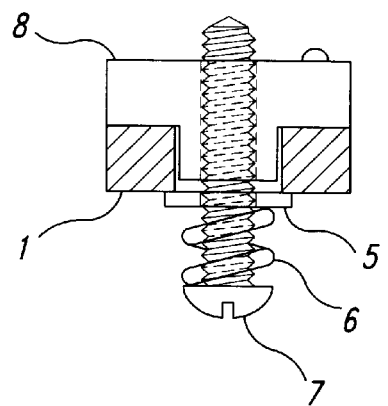
FIG. 6 illustrates a sectional view of the bar and detent bracket.
Figure 7:
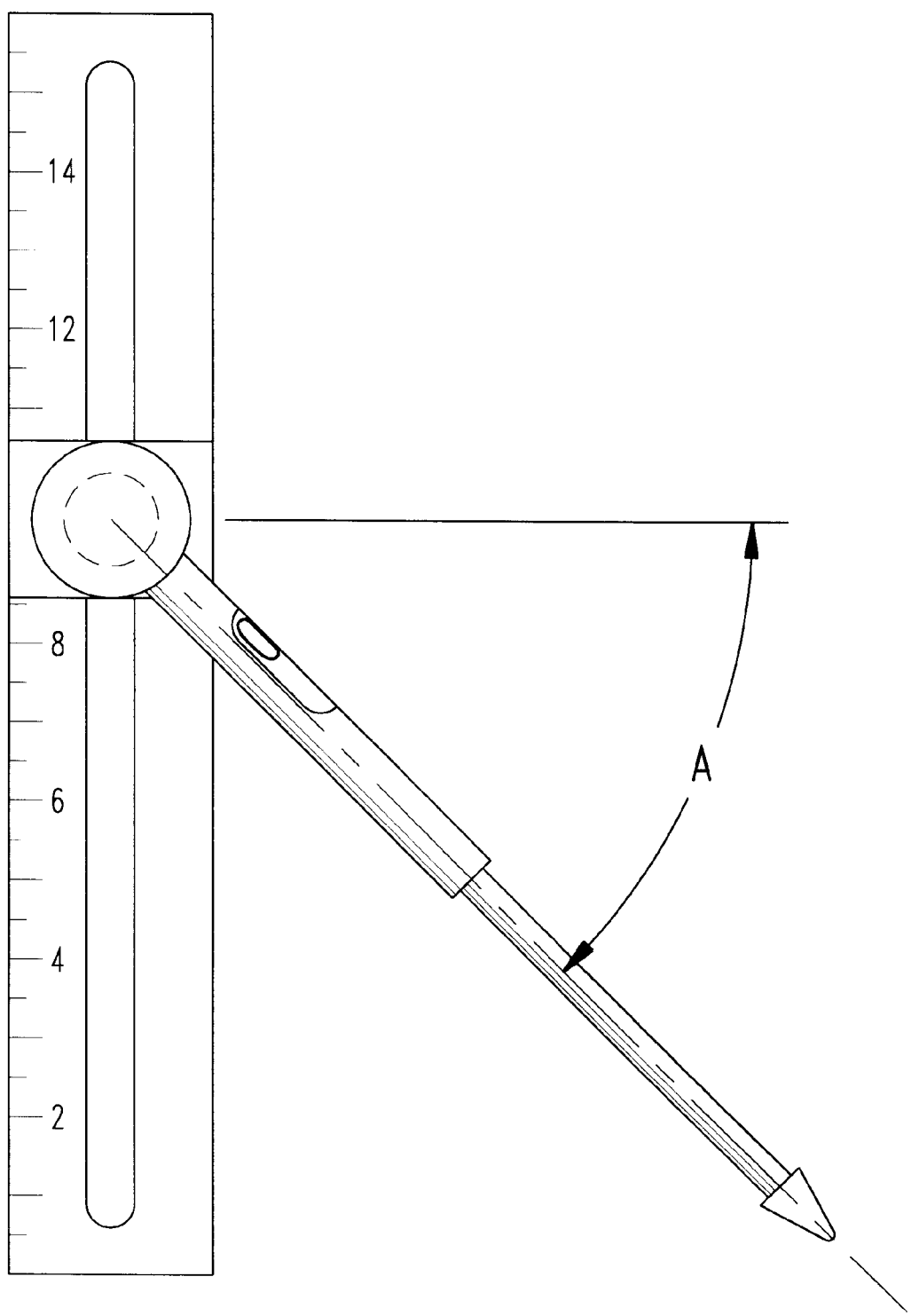
FIG. 7 illustrates a front view of the device with the telescoping pointer at an angle.

The detent bracket 8 and the base 10 are urged against each other by retaining screw 7 which is slidably received both in slot 9 and in hole 16 of bracket 8 and fixedly received in threaded hole 12 of pivoting base 10. As shown in FIG. 6 the retaining screw head is held in place by spring 6 and washer 5 on the side of the bar opposite that on which pivoting base 10 is located. Spring 6 biases the retaining screw head away from bar 1 such that pivoting base 10 and detent bracket 8 are held against bar 1 in a rigid fashion. Detent 13 intersects with one of depressions 11 to rigidly maintain the pivoting base and pointer 2 at a prescribed angle with respect to bar 1. The positioning of depressions 11 define where the detent will engage and therefore the angles at which pointer 2 may be held. Detent bracket 8 and pivoting base 10 together may be pushed along the length of the slot to adjust the height of the pointer. The force of spring 6 holds this assembly in its final position. Detent 13 may be disengaged from pivoting base 10 by pulling the pivoting base outward such that spring 6 is compressed. The pivoting base may be rotated about the axis of retaining screw 7 until the desired angle is reached at which point the pivoting base is released allowing spring 6 to force the rigid engagement of detent 13 and one of depressions 11.

To use the device, a physician first places the pointer at an angle, typically 45 degrees with respect to the bar, and the bar is placed parallel to the frame of a bed. The head of the bed is adjusted until the bubble-type indicating means indicates that the pointer is horizontal and the head of the bed is elevated at a 45 degree angle. Next, the pointer is placed at a 90 degree angle with respect to the bar by engaging the detent at the 90 degree recess and the bottom portion of the bar is positioned on the sternal angle such that the bubble-type indicating means indicates that the pointer is horizontal and the bar is vertical.

This is the critical step in the procedure in that an accurate estimate of the height of visible pulsations is based on the bar being in a vertical orientation and the pointer being in a horizontal orientation. The bubble-type indicating means enables the user to fix the pointer along a true horizontal and the 90 degree detent rigidly holds the pointer at a 90 degree angle with respect to the bar.

The telescoping distal end of the pointer is then extended to a position close to the patient's neck and the height of the pointer is adjusted by sliding the pivoting base along the length of the graduated bar. The distance between the sternal angle and the height of highest visible pulsations in the internal jugular vein is then gauged according to the graduated scale. The device enables a more accurate and repeatable estimation of central venous pressure in a non-invasive, risk-free manner, resulting in improved patient care.

The device is intended for external, non-invasive use only and should not come in contact with bodily fluids during the above-described procedure. For that reason the device may be used repeatedly without need of sterilization. Should the device come into contact with any form of contaminant a simple alcohol wash or other sterilization method would allow the immediate reuse of the device.

The device may be constructed of any rigid material which can withstand the stresses of the above-described procedure and maintain structural integrity to enable accurate estimations of central venous pressure. The device material should also be able to withstand a simple alcohol wash or other sterilization procedure. For example, the bar, the base, and the detent bracket may be made of rigid plastic. The interfitting cylinders of the pointer may be comprised of metal. Those skilled in the art will recognize many other materials which would meet the structural and durability requirements of the device.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

For example, the depressions 11 fixing the angle at which the telescoping pointer may be oriented with respect to the base can be set at various intervals. The method of estimating CVP described above may take place while the upper torso of the patient is at any substantial angle with respect to the the horizontal. Dr. Bates, in *A Guide to Physical Examination and History Taking*, indicates that the measurement may be taken with the patient elevated at an angle of fifteen degrees or more. The depressions may therefore be set at fifteen, thirty, forty-five, sixty, and ninety degrees or any combination thereof, or in any combination of angles between these such that the device is most useful as a diagnostic tool.

In other embodiments within the scope of the invention the mechanical means for linking the telescoping pointer to the bar may be comprised in various ways such that the pivoting base of the pointer is movable along the length of the bar and such that the pointer may be set at various angles with respect to the bar. For example, there may be an indentation rather than a slot in the bar such that the pivoting base of said pointer clamps onto the bar and is movable along the length of the bar.

The vertical measurement along the graduated scale affixed to the bar may be aided by an electronic sensor indicating the height of the pointer with respect to the bottom portion of the bar.

What is claimed is:

1. An apparatus for estimating central venous pressure comprising:

a substantially straight bar having a longitudinal axis and a bottom portion, the bottom portion being on the bar longitudinal axis, the bar having first cross-sectional area in a plane perpendicular to its longitudinal axis;

a pointer having an elongated base member with a longitudinal axis and having an elongated end member with a longitudinal axis, the end member having a second cross-sectional area in a plane perpendicular to its longitudinal axis which is less than the first cross-sectional area, the base member being mounted to the bar, the end member being supported for selected movement along a path substantially parallel to the base member longitudinal axis; and a horizontal indicator mounted on the pointer.

2. An apparatus according to claim 1 wherein:

the base member is movably mounted to the bar to permit the base member to be moved along the bar longitudinal axis and to be rotated relative to the bar longitudinal axis.

3. An apparatus according to claim 2, wherein the pointer is releasably fixed in a position relative to the bar by a plurality of detents.

4. An apparatus according to claim 1 wherein the end member is cylindrical with a diameter and is mounted coaxially with the base member longitudinal axis, the end member being selectively extendable from the base member in a telescoping manner; and wherein the bar is defined by a length, a first transverse dimension, and a second transverse dimension, the diameter of the end member being less than the larger of the first and second transverse dimensions.

5. An apparatus according to claim 1 wherein:

the horizontal indicator is mounted on the base member.

6. An apparatus according to claim 1, further comprising;

a cap attached to a distal end of the end member;

a slot formed in the bar substantially parallel to the bar longitudinal axis, the base member being movably mounted to the bar in the slot;

a pivot interposed between the base member and the bar to permit the pointer to be rotated relative to the bar longitudinal axis;

a plurality of detents located at the pivot to releasably fix the base member in a selected position; and a visible scale fixedly arranged along a length of the bar substantially parallel to the bar longitudinal axis.

7. An apparatus for estimating central venous pressure in a human patient having a neck and a sternal angle with the patient being situated in a reclining position and the neck being elevated from the sternal angle at a selected angle, the apparatus comprising:

an elongated bar having a longitudinal axis and a bottom portion, the bar having a first cross-sectional area in a plane perpendicular to its longitudinal axis, the bottom portion being on the bar longitudinal axis and positionable at or in contact with the sternal angle of the patient;

a pointer having an elongated base member with a longitudinal axis and having an elongated end member with a longitudinal axis, the end member having a second cross-sectional area in a plane perpendicular to its longitudinal axis which is less than the first cross-sectional area, the base member being mounted to the bar and supporting the end member, the end member being extendable from a retracted position to an extended position substantially parallel to the base member longitudinal axis a sufficient distance to position the end member at the neck of the patient when the bottom portion is positioned at the sternal angle of the patient and the pointer has a horizontal attitude; and a level indicator mounted on the pointer, the level indicator indicating when the pointer is in the horizontal attitude.

8. The apparatus of claim 7, wherein the bottom portion is sized to be placed in contact with the sternal angle when the pointer is directed toward the neck of the patient.

9. The apparatus of claim 8 wherein the end member is sized to extend a distance less than a horizontal distance between the sternal angle and the neck of the patient when the end member is in the retracted position, and the end member is sized to extend a distance substantially equal to the horizontal distance between the sternal angle and the neck of the patient when the end member is in the extended position with a horizontal attitude and when the bottom portion is in contact with the sternal angle and the bar extends from the sternal angle at a selected angle from a vertical dimension aligned with the sternal angle.

10. The apparatus of claim 9 wherein the end member includes a pointed end portion sized to be placed in contact with the neck of the patient when the base is in contact with the sternal angle and the end member is in the extended position between the bar and the neck of the patient.

11. The apparatus of claim 10 wherein the end member is cylindrical with a diameter and is supported in a coaxial relation with the base member longitudinal axis and is extendable from the base member in a telescoping fashion; and wherein the bar is defined by a length, a first transverse dimension, and a second transverse dimension, the diameter of the end member being less than the larger of the first and second transverse dimensions.

12. The apparatus of claim 11, further comprising:

a slot formed in the bar substantially parallel to the bar longitudinal axis, the base member being movably mounted to the bar in relation to the slot, the base member being movable along the slot;

a pivot mounted to the base member to permit the pointer to be rotated relative to the bar longitudinal axis, the pivot including a plurality of detents, the pointer being releasably fixed in a position relative to the bar longitudinal axis by the detents; and a visible scale arranged along a length of the bar substantially parallel to the bar longitudinal axis.

13. The apparatus of claim 7 wherein the base member is movably mounted to the bar to permit the pointer to be moved along the bar longitudinal axis and to be rotated relative to the bar longitudinal axis.

14. The apparatus of claim 7 wherein the level indicator is mounted on the base member.

* * * * *